(12) United States Patent
Zlotolow (10) Patent No.: US 10,117,689 B2
(45) Date of Patent: Nov. 6, 2018

(54) VARIABLE ANGLE BLADE PLATE SYSTEM AND METHOD

(71) Applicant: McGinley Engineered Solutions, LLC, Casper, WY (US)

(72) Inventor: Dan Zlotolow, Wyndmoor, PA (US)

(73) Assignee: McGinley Engineered Solutions, LLC, Casper, WY (US)

( * ) Notice: Subject to any disclaimer, the term of this patent is extended or adjusted under 35 U.S.C. 154(b) by 0 days.

(21) Appl. No.: 15/832,104

(22) Filed: Dec. 5, 2017

(65) Prior Publication Data

US 2018/0153595 A1    Jun. 7, 2018

Related U.S. Application Data

(63) Continuation of application No. 14/491,352, filed on Sep. 19, 2014, now Pat. No. 9,833,270.

(60) Provisional application No. 61/879,947, filed on Sep. 19, 2013.

(51) Int. Cl.
*A61B 17/80*    (2006.01)
*A61B 17/88*    (2006.01)

(52) U.S. Cl.
CPC ............ *A61B 17/809* (2013.01); *A61B 17/80* (2013.01); *A61B 17/8057* (2013.01); *A61B 17/8872* (2013.01)

(58) Field of Classification Search
CPC . A61B 17/80; A61B 17/8004; A61B 17/8014; A61B 17/8052; A61B 17/8061; A61B 17/809
See application file for complete search history.

(56) References Cited

U.S. PATENT DOCUMENTS

| | | | |
|---|---|---|---|
| 2,561,550 A | 7/1951 | Wright | |
| 4,651,724 A | 3/1987 | Berentey | |
| 4,683,878 A | 8/1987 | Carter | |
| 5,006,120 A * | 4/1991 | Carter | A61B 17/809 606/281 |
| 5,197,966 A | 3/1993 | Sommerkamp | |
| 5,586,985 A | 12/1996 | Putnam et al. | |
| 5,662,649 A | 9/1997 | Huebner | |
| 5,709,682 A | 1/1998 | Medoff | |
| 5,718,704 A | 2/1998 | Medoff | |
| 5,853,413 A | 12/1998 | Carter et al. | |
| 5,931,839 A | 8/1999 | Medoff | |
| 5,935,128 A | 8/1999 | Carter et al. | |
| 5,941,878 A | 8/1999 | Medoff | |
| 6,001,099 A | 12/1999 | Huebner | |
| 6,007,536 A * | 12/1999 | Yue | A61B 17/809 606/60 |
| 6,096,040 A | 8/2000 | Esser | |

(Continued)

FOREIGN PATENT DOCUMENTS

| | | |
|---|---|---|
| FR | 2650500 | 2/1991 |
| JP | 03930812 | 5/2004 |

(Continued)

*Primary Examiner* — Eric S Gibson
(74) *Attorney, Agent, or Firm* — Marsh Fischmann & Breyfogle LLP (57) ABSTRACT

A bone fixation system having a plate with an axle and a blade or "beam" configured to engage with the axle and reside proximate to a subchondral fragment of bone in upon installation of the plate. The beam is operable to rotate about the axle on the plate and reposition the subchondral fragment of bone.

13 Claims, 8 Drawing Sheets

(56) References Cited

U.S. PATENT DOCUMENTS

| | | | |
|---|---|---|---|
| 6,123,704 A | 9/2000 | Hajianpour | |
| 6,197,027 B1 | 3/2001 | Hajianpour | |
| 6,221,073 B1 | 4/2001 | Weiss | |
| 6,283,969 B1 | 9/2001 | Grusin | |
| 6,355,042 B2 | 3/2002 | Winquist et al. | |
| 6,358,250 B1 | 3/2002 | Orbay | |
| 6,364,882 B1 | 4/2002 | Orbay | |
| 6,379,359 B1 | 4/2002 | Dahners | |
| 6,440,135 B2 | 8/2002 | Orbay et al. | |
| 6,508,819 B1 | 1/2003 | Orbay | |
| 6,585,736 B2 | 7/2003 | Haijanpour | |
| 6,629,976 B1 | 10/2003 | Gnos et al. | |
| 6,635,059 B2 | 10/2003 | Randall et al. | |
| 6,702,817 B2 | 3/2004 | Beger et al. | |
| 6,706,046 B2 | 3/2004 | Orbay et al. | |
| 6,712,820 B2 | 3/2004 | Orbay | |
| 6,730,090 B2 | 5/2004 | Orbay et al. | |
| 6,755,831 B2 | 6/2004 | Putnam et al. | |
| 6,767,351 B2 | 7/2004 | Orbay et al. | |
| 6,893,444 B2 | 5/2005 | Orbay | |
| 6,926,720 B2 | 8/2005 | Casteneda | |
| 7,001,388 B2 * | 2/2006 | Orbay | A61B 17/8061 606/286 |
| 7,090,676 B2 | 8/2006 | Huebner | |
| 7,137,987 B2 | 11/2006 | Patterson et al. | |
| 7,153,309 B2 | 12/2006 | Huebner et al. | |
| 7,160,302 B2 | 1/2007 | Warburton | |
| 7,189,237 B2 | 3/2007 | Huebner | |
| 7,195,633 B2 | 3/2007 | Medoff | |
| 7,229,445 B2 * | 6/2007 | Hayeck | A61B 17/74 606/70 |
| 7,250,053 B2 | 7/2007 | Orbay | |
| 7,267,678 B2 | 9/2007 | Medoff | |
| 7,282,053 B2 | 10/2007 | Orbay | |
| 7,294,130 B2 | 11/2007 | Orbay | |
| 7,299,561 B2 | 11/2007 | Castenda | |
| 7,316,687 B2 * | 1/2008 | Aikins | A61B 17/1668 606/70 |
| 7,341,589 B2 | 3/2008 | Weaver et al. | |
| 7,367,977 B2 | 5/2008 | Estada, Jr. | |
| 7,527,639 B2 | 5/2009 | Orbay et al. | |
| 7,537,596 B2 | 5/2009 | Jensen | |
| 7,537,604 B2 | 5/2009 | Huebner | |
| 7,578,825 B2 * | 8/2009 | Huebner | A61B 17/683 606/104 |
| 7,588,577 B2 | 9/2009 | Fencl et al. | |
| 7,603,192 B2 | 10/2009 | Martin et al. | |
| 7,604,657 B2 | 10/2009 | Orbay et al. | |
| 7,635,381 B2 | 12/2009 | Orbay | |
| 7,648,508 B2 | 1/2010 | Lutz et al. | |
| 7,686,808 B2 | 3/2010 | Orbay et al. | |
| 7,695,502 B2 | 4/2010 | Orbay et al. | |
| 7,719,260 B2 | 5/2010 | Uchida et al. | |
| 7,727,264 B2 | 6/2010 | Orbay et al. | |
| 7,740,634 B2 | 6/2010 | Orbay | |
| 7,771,433 B2 | 8/2010 | Orbay et al. | |
| 7,771,457 B2 | 8/2010 | Kay et al. | |
| 7,780,711 B2 | 8/2010 | Orbay et al. | |
| 7,799,061 B2 | 9/2010 | Kay et al. | |
| 7,857,838 B2 | 12/2010 | Orbay | |
| 7,867,260 B2 | 1/2011 | Meyer | |
| 7,887,569 B2 | 2/2011 | Frigg | |
| 7,905,909 B2 | 3/2011 | Orbay | |
| 7,951,176 B2 | 5/2011 | Grady, Jr. | |
| 7,951,178 B2 | 5/2011 | Jensen | |
| 8,021,402 B2 | 9/2011 | Martin | |
| 8,043,297 B2 | 10/2011 | Grady, Jr. | |
| 8,062,296 B2 | 11/2011 | Orbay | |
| 8,100,952 B2 | 1/2012 | Matityahu | |
| 8,114,081 B2 | 2/2012 | Kohut | |
| 8,147,530 B2 | 4/2012 | Strnad | |
| 8,172,886 B2 | 5/2012 | Castaneda | |
| 8,394,098 B2 | 3/2013 | Orbay | |
| 8,394,130 B2 | 3/2013 | Orbay | |
| 8,579,899 B2 * | 11/2013 | Ahmadi | A61B 17/1721 606/280 |
| 8,591,554 B2 * | 11/2013 | Raven, III | A61B 17/8061 606/286 |
| 8,603,148 B2 * | 12/2013 | Raven, III | A61B 17/8061 606/286 |
| 8,926,675 B2 | 1/2015 | Leung | |
| 9,066,766 B2 * | 6/2015 | Raven, III | A61B 17/8061 |
| 9,295,506 B2 * | 3/2016 | Raven, III | A61B 17/80 |
| 9,833,270 B2 * | 12/2017 | Zlotolow | A61B 17/809 |
| 2003/0040748 A1 * | 2/2003 | Aikins | A61B 17/1668 606/70 |
| 2003/0153918 A1 | 8/2003 | Putnam | |
| 2004/0102775 A1 | 5/2004 | Huebner | |
| 2004/0111090 A1 | 6/2004 | Dahners | |
| 2004/0153073 A1 | 8/2004 | Orbay | |
| 2004/0193155 A1 | 9/2004 | Castenda | |
| 2004/0193164 A1 | 9/2004 | Orbay | |
| 2004/0193165 A1 | 9/2004 | Orbay | |
| 2004/0220570 A1 | 11/2004 | Frigg | |
| 2004/0260291 A1 | 12/2004 | Jensen | |
| 2004/0260292 A1 | 12/2004 | Orbay | |
| 2004/0260293 A1 | 12/2004 | Orbay et al. | |
| 2004/0260294 A1 | 12/2004 | Orbay | |
| 2004/0260295 A1 | 12/2004 | Orbay et al. | |
| 2005/0010226 A1 | 1/2005 | Grady, Jr. | |
| 2005/0065522 A1 | 3/2005 | Orbay | |
| 2005/0065523 A1 | 3/2005 | Orbay | |
| 2005/0065524 A1 | 3/2005 | Orbay | |
| 2005/0085818 A1 | 4/2005 | Huebner | |
| 2005/0107795 A1 | 5/2005 | Morris et al. | |
| 2005/0143736 A1 * | 6/2005 | da Frota Carrera | A61B 17/8004 606/60 |
| 2005/0154392 A1 | 7/2005 | Medoff | |
| 2005/0159747 A1 | 7/2005 | Orbay | |
| 2005/0171544 A1 * | 8/2005 | Falkner, Jr. | A61B 17/1728 606/281 |
| 2005/0234458 A1 | 10/2005 | Huebner | |
| 2005/0240186 A1 | 10/2005 | Orbay | |
| 2006/0009771 A1 | 1/2006 | Orbay | |
| 2006/0015101 A1 | 1/2006 | Warburton et al. | |
| 2006/0041260 A1 | 2/2006 | Orbay | |
| 2006/0089648 A1 | 4/2006 | Masini | |
| 2006/0100624 A1 | 5/2006 | Orbay | |
| 2006/0136063 A1 * | 6/2006 | Zeegers | A61B 17/0642 623/17.14 |
| 2006/0161156 A1 | 7/2006 | Orbay et al. | |
| 2006/0161158 A1 | 7/2006 | Orbay | |
| 2006/0173458 A1 | 8/2006 | Forstein et al. | |
| 2006/0200145 A1 | 9/2006 | Kay | |
| 2006/0200151 A1 | 9/2006 | Ducharme et al. | |
| 2006/0259039 A1 | 11/2006 | Pitkanen et al. | |
| 2007/0043366 A1 | 2/2007 | Pfefferle et al. | |
| 2007/0055253 A1 | 3/2007 | Orbay | |
| 2007/0083202 A1 | 4/2007 | Eli Running et al. | |
| 2007/0088360 A1 | 4/2007 | Orbay | |
| 2007/0233112 A1 | 10/2007 | Orbay | |
| 2008/0021477 A1 | 1/2008 | Strnad et al. | |
| 2008/0027439 A1 | 1/2008 | Sasing | |
| 2008/0091198 A1 | 4/2008 | Libel et al. | |
| 2009/0054762 A1 * | 2/2009 | Burgkart | A61B 17/152 600/424 |
| 2009/0062862 A1 | 3/2009 | Perrow | |
| 2009/0105832 A1 * | 4/2009 | Allain | A61B 17/0642 623/17.16 |
| 2009/0228047 A1 | 9/2009 | Derouet et al. | |
| 2009/0234359 A1 | 9/2009 | Onoue et al. | |
| 2011/0152864 A1 * | 6/2011 | Ahmadi | A61B 17/1721 606/71 |
| 2011/0276097 A1 * | 11/2011 | Raven, III | A61B 17/8061 606/284 |
| 2011/0307019 A1 * | 12/2011 | Raven, III | A61B 17/8061 606/289 |
| 2012/0172933 A1 * | 7/2012 | Raven, III | A61B 17/8061 606/286 |
| 2012/0203228 A1 * | 8/2012 | Raven, III | A61B 17/8061 606/70 |

(56) References Cited

U.S. PATENT DOCUMENTS

| | | | |
|---|---|---|---|
| 2013/0041375 A1* | 2/2013 | Fierlbeck | A61B 17/8061 606/71 |
| 2013/0226300 A1* | 8/2013 | Chataigner | A61F 2/442 623/17.16 |
| 2013/0245696 A1* | 9/2013 | Raven, III | A61B 17/8061 606/280 |
| 2014/0094804 A1* | 4/2014 | Raven, III | A61B 17/8061 606/70 |
| 2015/0134010 A1* | 5/2015 | Zlotolow | A61B 17/80 606/281 |
| 2015/0320568 A1* | 11/2015 | Ameil | A61F 2/447 623/17.13 |

FOREIGN PATENT DOCUMENTS

| | | |
|---|---|---|
| JP | 2007190115 | 8/2007 |
| JP | 2008206789 | 9/2008 |
| WO | 2010061410 A1 | 6/2010 |

\* cited by examiner

VARIABLE ANGLE BLADE PLATE SYSTEM AND METHOD

CROSS-REFERENCE TO RELATED APPLICATION

This patent application is a continuation of U.S. patent application Ser. No. 14/491,352 filed on Sep. 19, 2014 entitled "VARIABLE ANGLE BLADE PLATE SYSTEM AND METHOD", which claims the benefit of U.S. Provisional Patent Application Ser. No. 61/879,947 titled VARIABLE ANGLE BLADE PLATE SYSTEM AND METHOD, and filed Sep. 19, 2013, the entire contents of which are herein incorporated by reference in their entirety.

BACKGROUND

1. Field

The present inventive concept generally pertains to bone fractures, and more particularly, to a system for treating bone fractures.

2. Discussion of Related Art

A bone fracture is a medical condition in which there is a break in a bone. In some circumstances, a bone fracture can be the result of high force impact or stress. Bone fractures may be classified in a variety of ways. For example, fractures may be classified anatomically. Anatomical classifications may begin with specifying the involved body part, such as the skull, spine, ribs, sternum, shoulder, arm, hand, pelvis, femur, patella, lower leg, or foot. Within each anatomical classification, fractures may be classified based on a more specific localization. For example, arm fractures may be categorized into humerus fractures, ulnar fractures, and radius fractures. Anatomical classifications may also have additional definition criteria that distinguish between different types of fractures at the same location. For example, radius fractures may include various types of distal-radius fractures.

SUMMARY

The present inventive concept described herein provides a unique bone fixation system for treating bone fractures. The bone fixation system of the present inventive concept includes a plate with an axle and a blade or "beam" configured to engage with the axle and reside proximate to a subchondral fragment of bone in upon installation of the plate. The beam is operable to rotate about the axle on the plate and reposition the subchondral fragment of bone.

The various embodiments of the present inventive concept described herein provide numerous technical advantages. For example, the present inventive concept can be used to treat different classes of fractures, such as but not limited to different classes of radial and ulnar fractures, proximal tibial fractures, distal tibial fractures, acetabular fractures, proximal femoral fractures, distal femoral fractures, fracture malunions, and fracture non-unions. Further, the present inventive concept can be used to restore a subchondral fragment to its original position. Still further, the present inventive concept can be used to alter the angulation of a fracture fragment relative to another fracture fragment. Each embodiment of the present inventive concept may include none, some, or all of the above advantages and it is foreseen that one or more other advantages may be readily apparent to one skilled in the art having viewed the figures, descriptions, and/or claims included herein. The beam of the present inventive concept includes numerous advantages over conventional designs disclosed in, for example, U.S. Pat. No. 8,603,148 titled "SYSTEM FOR TREATING BONE FRACTURES" and filed on May 5, 2011, which is incorporated herein by reference in its entirety. Among other improvements, the system of the present inventive concept advantageously causes rotation of the beam to reposition and/or reduce fracture fragments, thereby providing significantly more robust beam retention on the plate relative to conventional designs.

The aforementioned may be achieved in one aspect of the present inventive concept by providing a bone fixation system operable to alter angulation of a fracture fragment of a bone. The system may include a bone fixation plate having at least one beam engagement feature, and/or an elongated beam having an end portion with (i) a plate engagement feature operable to rotatably engage the at least one beam engagement feature of the plate, (ii) at least one bone engagement feature operable to engage a portion of a bone, and/or (iii) a retention feature operable to prevent detachment of the beam from the plate.

The beam may include a receiver operable to receive a tool. The receiver may be a hole extending at least partially through the beam. The hole may be sized and shaped to threadedly receive a terminally-threaded rod, e.g., inserter rod and/or extractor rod. The rod may be part of a tool configured to facilitate engagement and/or disengagement of the beam to a portion of the plate or cause the beam and plate to engage and/or disengage from each other.

The tool may include an internal portion and/or an external portion, relative to each other, that are rotatable relative to each other to cause engagement and/or disengagement of the beam with the rod. The tool may include two external portions that are rotatable relative to each other to cause engagement and/or disengagement of the beam with the rod. The external portion(s) may be at least partially visible with a visible portion being graspable by a user. The at least one of the internal and external portions of the rod may include a feature operable to engage a portion of the beam. The tool may include an exterior shaft that surrounds a portion of the rod. The shaft may include a concave portion configured to abuttingly engage a convex portion of the beam.

The bone engagement feature may be operable to at least partially penetrate the portion of the bone. The plate may include an opening operable to receive a positioner. The opening may extend through the plate at an angle that is oblique to a plane defined by a surface of the plate so as to direct the positioner toward an end of the plate having the at least one beam engagement feature. The positioner may be a screw operable to threadably advance through the opening, penetrate a bone, and abuttingly engage a portion of the beam, and cause the beam to pivot relative to the plate so as to move the bone to a desired position, all while threadably advancing through the opening.

The plate may include a retention mechanism operable to prevent disengagement of the beam with the plate unless the mechanisms biased toward the portion of the plate by the rod. The plate may be operable to allow rotation of the beam about the portion of the plate when the positioner is moved with respect to the opening in the plate.

The at least one beam engagement feature of the plate may be an axle that defines an axis of rotation. The at least one bone engagement feature and the retention feature of the beam may be spaced from each other along or about a curved portion of the beam. The curved portion of the beam may be operable to slidably or rotatable engage the axle to permit rotation of the beam relative to the plate about the axis of rotation. The plate may include two beam engagement features that are elongated extended in a direction substantially to each other on an end of the plate.

The aforementioned may be achieved in one aspect of the present inventive concept by providing a method of repositioning a displaced bone fragment. The method may include the step of (i) attaching a rod to a beam, (ii) causing the beam to securely engage a portion of a bone fixation plate using the rod, and/or (iii) causing the beam to rotate about the portion of the plate by advancing a positioner at least partially through an opening in the plate. The rod may be configured to be at least partially received by the beam. The rod may be part of a tool having internal and external portions that are rotatable relative to each other to affect engagement and disengagement of the beam with the rod.

The tool may include a shaft that surrounds portion of the rod. The tool may include a concave portion configured to abuttingly engage a convex portion of the beam. The plate may include a retention mechanism operable to prevent disengagement of the beam with the plate unless the mechanism is biased in a direction, e.g., toward a portion of the plate by the rod. The beam may include a bone fragment-grip feature configured to (i) pierce a bone fragment as the beam rotates relative to the plate, and/or (ii) provide fixation between the beam and the bone fragment.

The aforementioned may be achieved in one aspect of the present inventive concept by providing a method of treating a bone fracture by altering angulation of a fracture fragment of a bone using a bone fixation system. The method may include the steps of (i) securing a beam to a bone fixation plate, (ii) securing the plate to the fracture fragment of the bone, (iii) advancing a screw through the plate, to abut the beam, and/or (iv) causing the beam to pivot with respect to the plate by further advancing the screw through the plate.

The plate may have at least one beam engagement feature used for securing the beam to the plate. The beam may have an end portion with (i) a plate engagement feature operable to rotatably engage the at least one beam engagement feature of the plate, (ii) at least one bone engagement feature operable to engage a portion of a bone, and/or (iii) a retention feature operable to prevent detachment of the beam from the plate.

The beam may include a receiver operable to receive a tool. The receiver may be a hole extending at least partially through the beam. The hole may be sized and shaped to threadedly receive a terminally-threaded inserter/extractor rod of the tool. The rod may be configured to facilitate the securing of the beam to the plate. The tool may include internal and external portions that are rotatable relative to each other to affect the engagement and/or disengagement of the beam with the rod. The tool may include a shaft that surrounds a portion of the rod. The tool may include a concave portion configured to abuttingly engage a convex portion of the beam.

The bone engagement feature may be operable to at least partially penetrate portion of the bone. The plate may include an opening operable to receive a positioner. The opening may extend through the plate at an angle that is oblique to a plane defined by a surface of the plate so as to direct the positioner toward an end of the plate having the at least one beam engagement feature. The positioner may be a screw operable to threadably advance through the opening and engage a portion of the beam, and cause the beam to pivot relative to the plate.

The plate may include a retention mechanism operable to prevent disengagement of the beam with the plate unless the mechanism is biased toward the portion of the plate by the rod. The plate may be operable to allow rotation of the beam about the portion of the plate when the positioner is moved with respect to the opening in the plate. The at least one beam engagement feature of the plate may be an axle that defines an axis of rotation. The at least one bone engagement feature and the retention feature of the beam are spaced from each other about a curved portion of the beam that is operable to rotatably engage the axle to permit rotation of the beam relative to the plate about the axis of rotation. The plate may include two beam engagement features that are elongated and extend in a direction substantially parallel to each other on an end of the plate.

Additional aspects, advantages, and utilities of the present inventive concept will be set forth in part in the description which follows and, in part, will be obvious from the description, or may be learned by practice of the present inventive concept.

The foregoing is intended to be illustrative and is not meant in a limiting sense. Many features and subcombinations of the present inventive concept may be made and will be readily evident upon a study of the following specification and accompanying drawings comprising a part thereof. These features and subcombinations may be employed without reference to other features and subcombinations.

BRIEF DESCRIPTION OF THE DRAWINGS

The present inventive concept is described in detail below with reference to the attached drawing figures, wherein.

The drawing figures do not limit the present inventive concept to the specific examples disclosed and described herein. The drawings are not necessarily to scale, emphasis instead being placed upon clearly illustrating the principles of the present inventive concept.

DETAILED DESCRIPTION

The following detailed description references the accompanying drawings that illustrate the present inventive concept. The illustrations and description are intended to describe aspects of the present inventive concept in sufficient detail to enable those skilled in the art to practice the present inventive concept. Other components can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

In this description, references to "one embodiment," "an embodiment," or "embodiments" mean that the feature or features being referred to are included in at least one embodiment of the present inventive concept. Separate references to "one embodiment," "an embodiment," or "embodiments" in this description do not necessarily refer to the same, embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present inventive concept can include a variety of combinations and/or integrations of the embodiments described herein.

Turning to FIGS. 1-36, a receiver in the form of threaded hole 1 is provided through a beam 5 that is sized and shaped for the purpose of inserting, extracting, and articulating the beam 5 from and/or about a bone fixation plate 14. The hole 1 is sized and shaped to matably receive a terminally threaded inserter central rod 15 and/or a terminally threaded extractor central rod 8 of an inserter/extractor device 13, it is foreseen that the rods 8, 15 may be simultaneously present on the same device 13, alternately present on the same device 13 as illustrated by the figures, e.g., "bits" that are removably attachable to the device 13, or permanently attached to different ones of the device 13, without deviating from the scope of the present inventive concept.

Figures 19, 20:
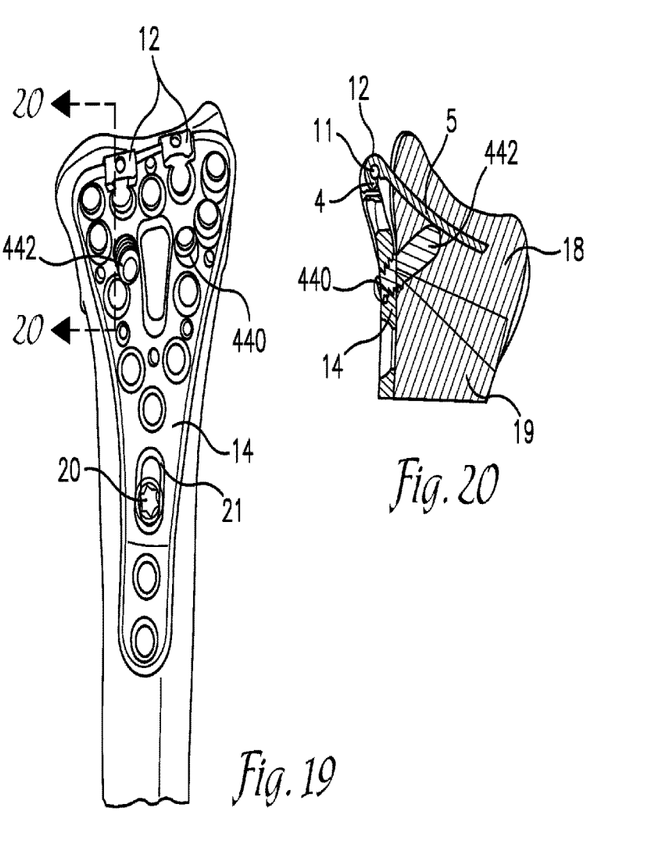
FIG. 19 is a magnified perspective view of portion "A" of FIG. 18 of the beam and the plate of the present inventive concept illustrated in FIG. 18.
FIG. 20 is a cross-section view of the beam and the plate of the present inventive concept illustrated in FIG. 18 taken along line E-E.
Figures 21, 22, 23, 24:
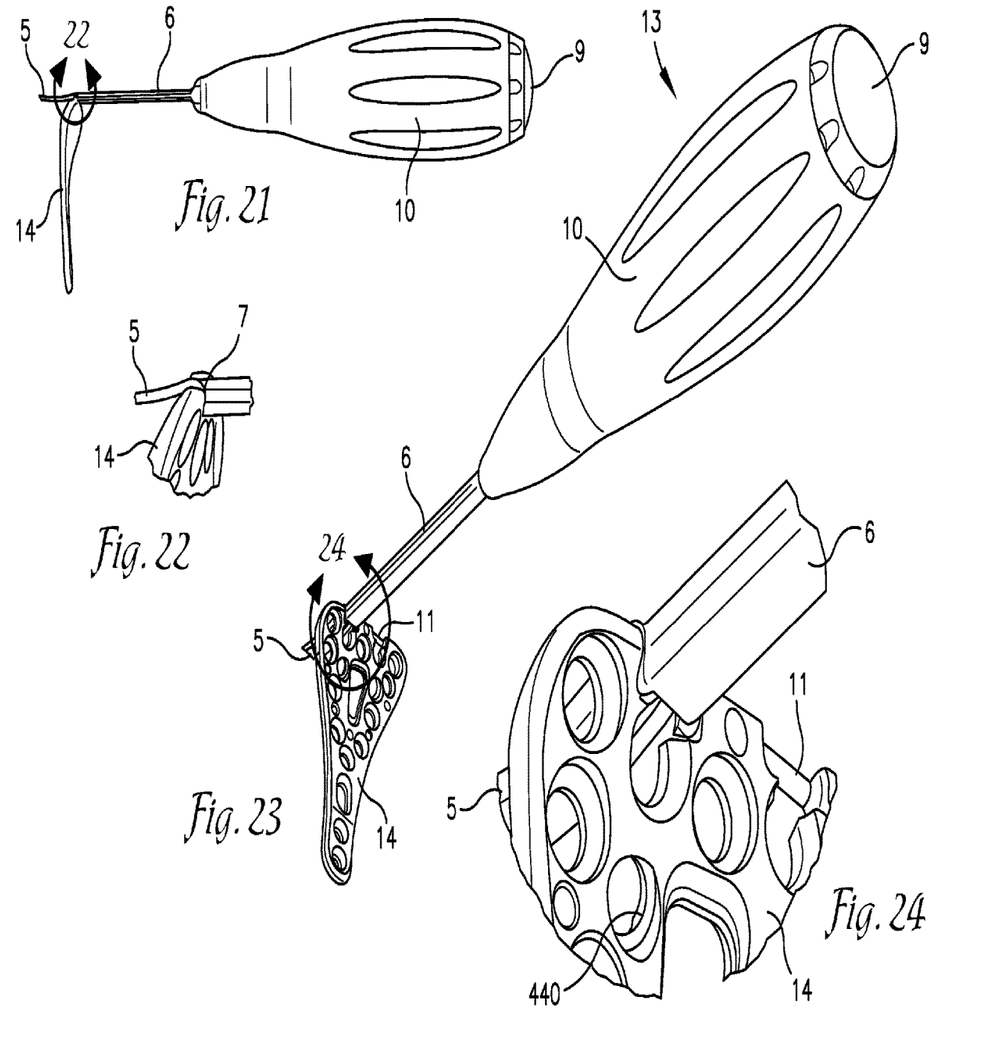
FIG. 21 is a right side view of a beam, a plate, and an inserter/extractor device of the present inventive concept.
FIG. 22 is a magnified perspective view of portion "H" of FIG. 21 of the beam, the plate, and the inserter/extractor device of the present inventive concept illustrated in FIG. 21.
FIG. 23 is a perspective view of the beam, the plate, and the inserter/extractor device of the present inventive concept illustrated in FIG. 21.
FIG. 24 is a magnified perspective view of portion "B" of FIG. 23 of the beam, the plate, and the inserter/extractor device of the present inventive concept illustrated in FIG. 23.
Figures 25, 26:
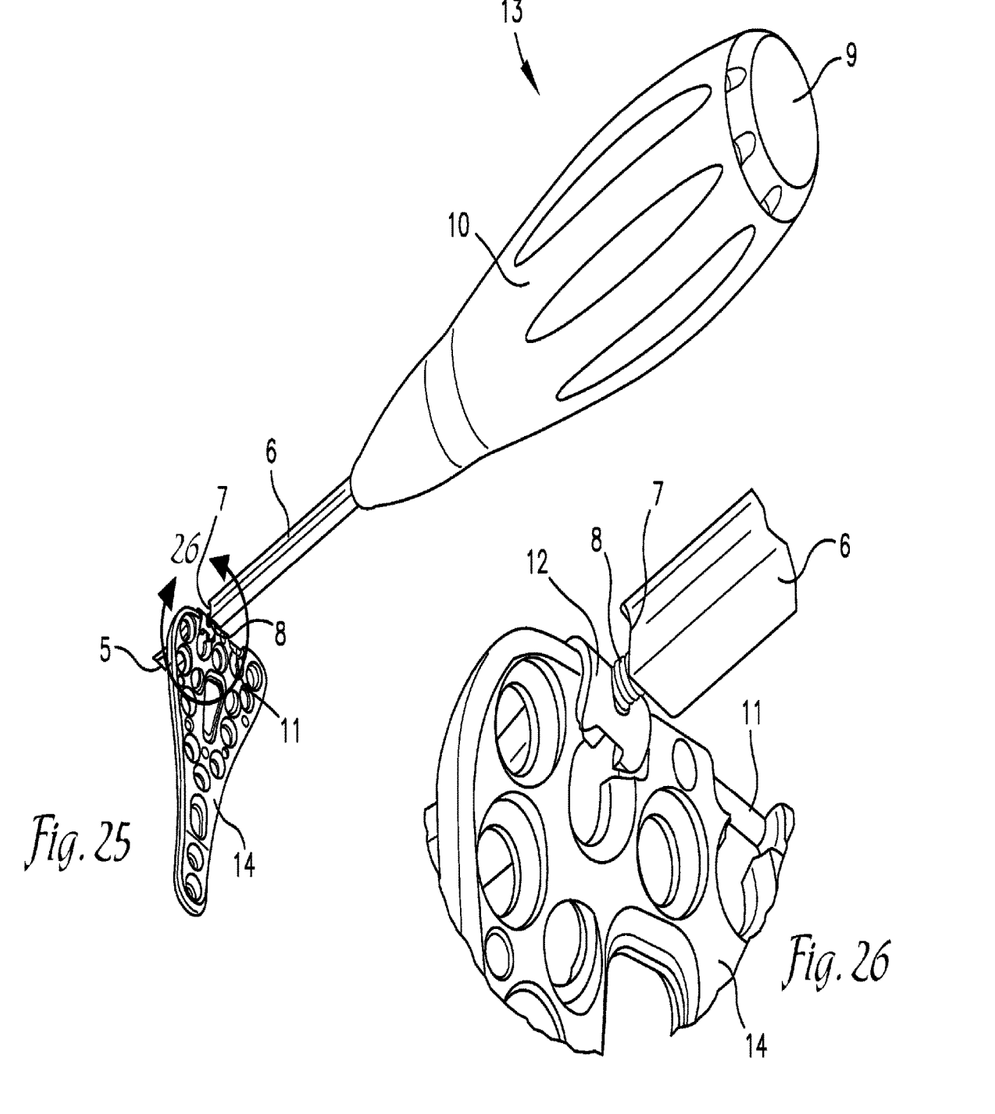
FIG. 25 is a perspective view of the beam, the plate, and the inserter/extractor device of the present inventive concept illustrated in FIG. 21.
FIG. 26 is a magnified perspective view of portion "C" of FIG. 25 of the beam, the plate, and the inserter/extractor device of the present inventive concept illustrated in FIG. 25.
Figures 27, 28, 29:
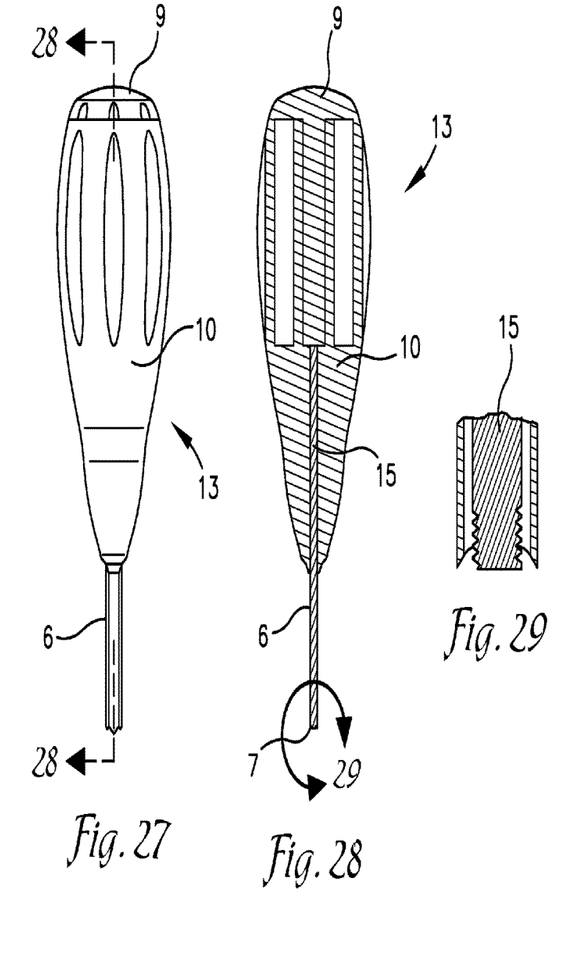
FIG. 27 is side view of an inserter device of the present inventive concept.
FIG. 28 is a cross-section view of the inserter device of the present inventive concept illustrated in FIG. 27 taken along line A-A.
FIG. 29 is a magnified side view of portion "C" of FIG. 28 of the inserter device of the present inventive concept illustrated in FIG. 28.
Figures 30, 31:
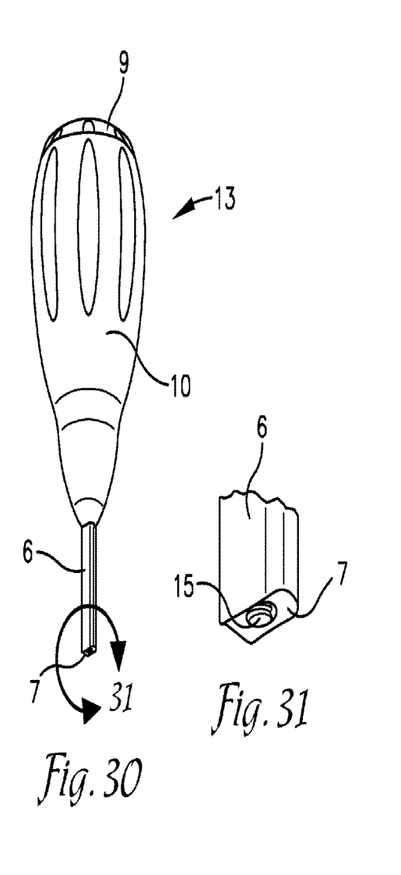
FIG. 30 is perspective view of the inserter device of the present inventive concept illustrated in FIG. 27.
FIG. 31 is a magnified perspective view of portion "D" of FIG. 30 of the inserter device of the present inventive concept illustrated in FIG. 30.
Figures 32, 33, 34:
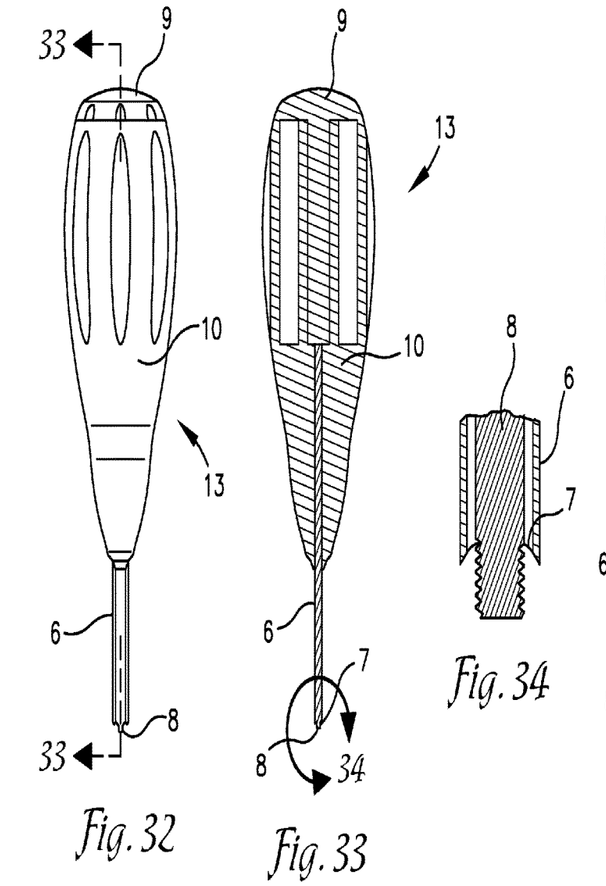
FIG. 32 is side view of an extractor device of the present inventive concept.
FIG. 33 is a cross-section view of the extractor device of the present inventive concept illustrated in FIG. 32 taken along line C-C.
FIG. 34 is a magnified side view of portion "D" of FIG. 33 of the extractor device of the present inventive concept illustrated in FIG. 33.
Figures 35, 36:
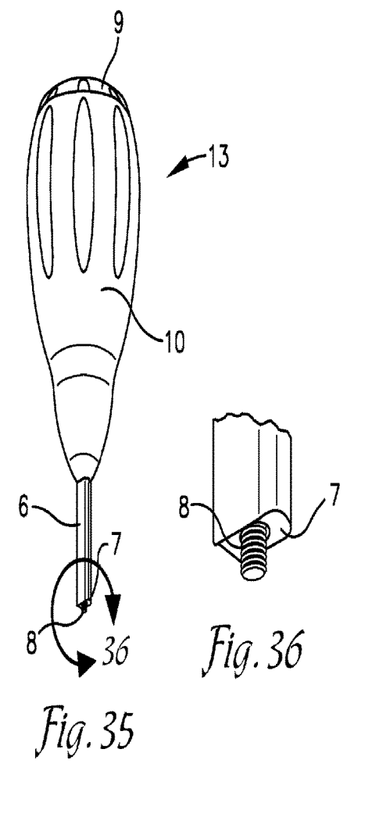
FIG. 35 is perspective view of the extractor device of the present inventive concept illustrated FIG. 32.
FIG. 36 is a magnified perspective view of portion "E" of FIG. 35 of the extractor device of the present inventive concept illustrated in FIG. 35.

The inserter and extractor central rods 15, 8 of the inserter/extractor device 13 are configured to screw into the threaded hole 1 to engage the inserter/extractor device 13 onto the beam 5. The inserter central rod 15 only has threads matching a length of a thread distance of the hole 1. The inserter central rod 15 is permanently attached to manual rotation device 9. A length of the inserter central rod 15 is only long enough to fully engage all of the threads of the hole 1 before the manual rotation device 9 of the inserter central rod 15 abuts a handle 10 of the inserter/extractor device 13. Once the manual rotation device 9 abuts the handle 10 of the inserter/extractor device 13, the central rod 8 and/or 15 is not able to advance any further. The beam 5 is then engaged with and onto the inserter/extractor device 13. A shaft 6 of the inserter/extractor device shaft 13 has a concave surface 7 that matches a convex surface 12 of the beam 5. When the concave surface 7 abuts the convex surface 12, and the inserter central rod 15 is terminally threaded into the threaded hole 1 of the beam 5, the beam 5 is affixed to the inserter/extractor device 13. The inserter/extractor device 13 is operable to guide the beam 5 into position and advance the beam 5 onto either axle 11 of the plate 14 located on either side of one end of the plate 14, as illustrated in FIG. 19. Once the beam 5 engages the axle 11, axle retention feature 3 of cantilever spring mechanism 2 prevents the beam 5 from disengaging or otherwise detaching from the axle 11. The cantilever spring mechanism 2 is resilient and is able to flex when engaging the axle 11 and then lock the axle 11 into a curved portion between the cantilever spring mechanism 2 and a bone grip feature 4 on either side of the beam 5.

The manual rotation device 9 can the be rotated in an opposite direction to unthread the inserter central rod 15 from the beam 5 threaded hole 1. Once the beam 5 is disengaged from the inserter/extractor device 13, but remains engaged to the axle 11 via the cantilever spring mechanism 2, the beam 5 is now able to rotate around the axle 11 without disengaging from the plate 14.

Figure 1:
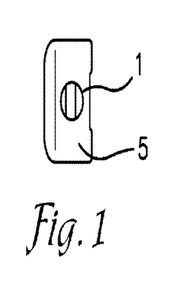
FIG. 1 is top plan view of a beam of the present inventive concept.
Figure 2:
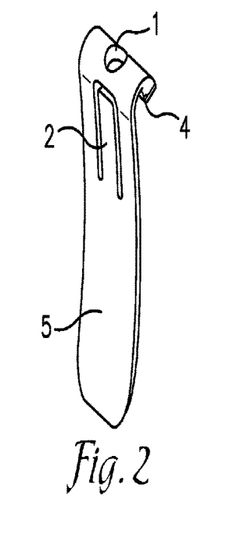
FIG. 2 is a perspective view of the beam of the present inventive concept illustrated in FIG. 1.
Figure 3:
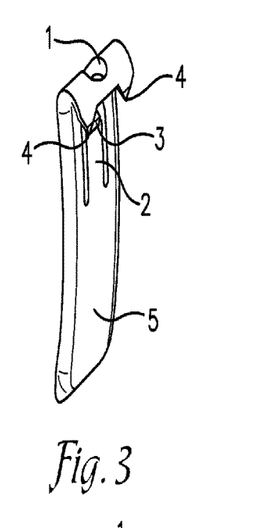
FIG. 3 is a perspective view of the beam of the present inventive concept illustrated in FIG. 1.
Figure 4:
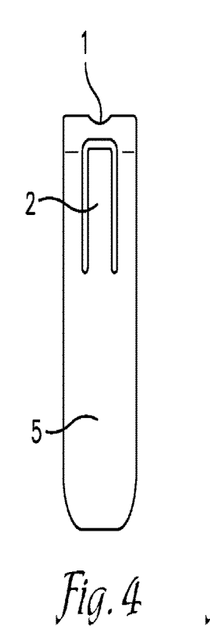
FIG. 4 is a front side view of the beam of the present inventive concept illustrated in FIG. 1.
Figure 5:
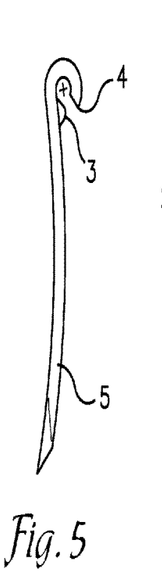
FIG. 5 is a right side view of the beam of the present inventive concept illustrated in FIG. 1.
Figure 6:
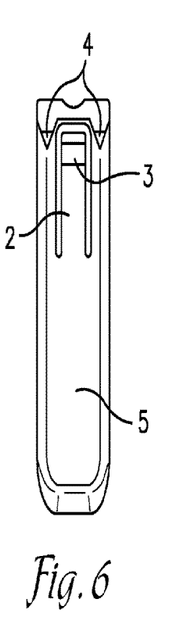
FIG. 6 is a rear side view of the beam of the present inventive concept illustrated in FIG. 1.
Figure 7:
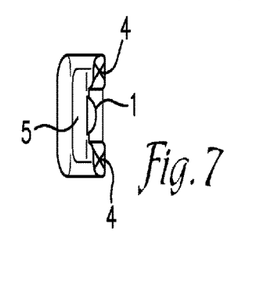
FIG. 7 is a bottom view of the beam of the present inventive concept illustrated in FIG. 1.
Figures 8, 9:
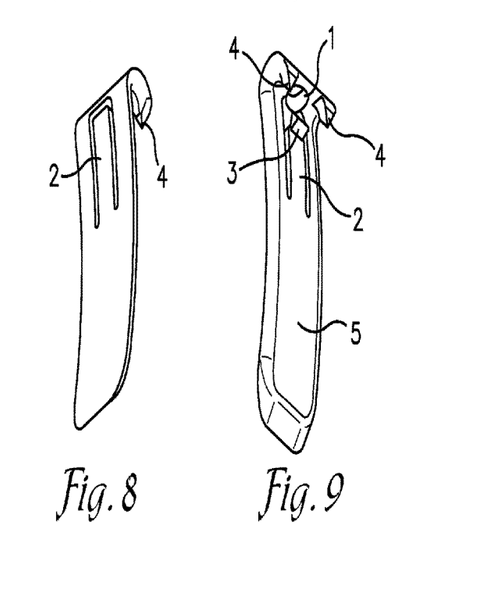
FIG. 8 is a perspective view of the beam of the present inventive concept illustrated in FIG. 1.
FIG. 9 is a perspective view of the beam of the present inventive concept illustrated in FIG. 1.
Figure 10:
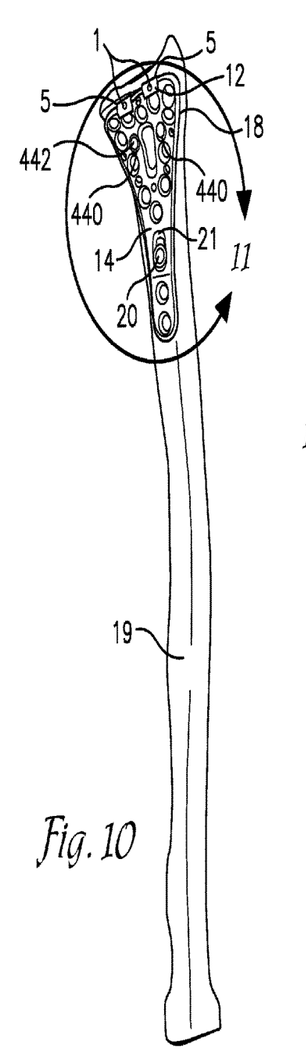
FIG. 10 is a perspective view of the beam illustrated in FIG. 1 in use with a plate of the present inventive concept and mounted to a bone fragment.
Figures 11, 12:
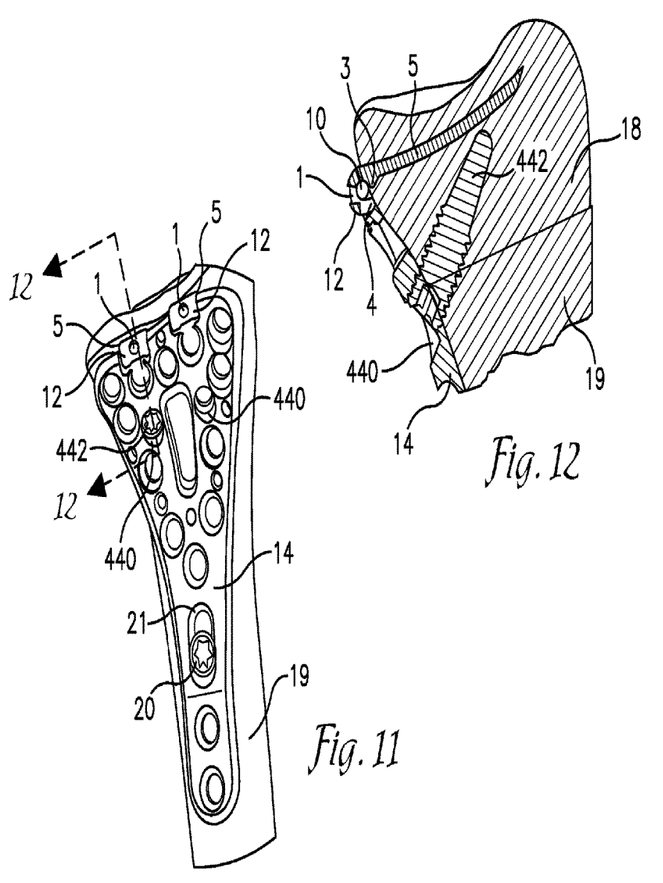
FIG. 11 is a magnified perspective view of portion "A" of FIG. 10 of the beam and the plate of the present inventive concept illustrated in FIG. 10.
FIG. 12 is a cross-section view of the beam and the plate of the present inventive concept illustrated in FIG. 10 taken along line D-D.
Figure 13:
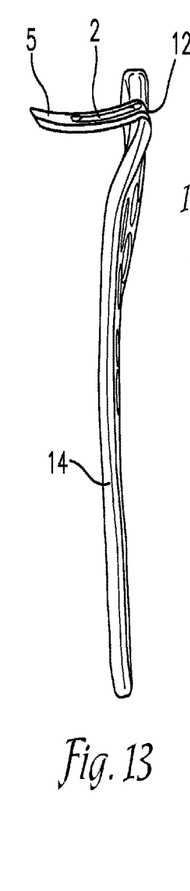
FIG. 13 is a right side view of a beam and a plate of the present inventive concept.
Figures 14, 15, 16, 17:
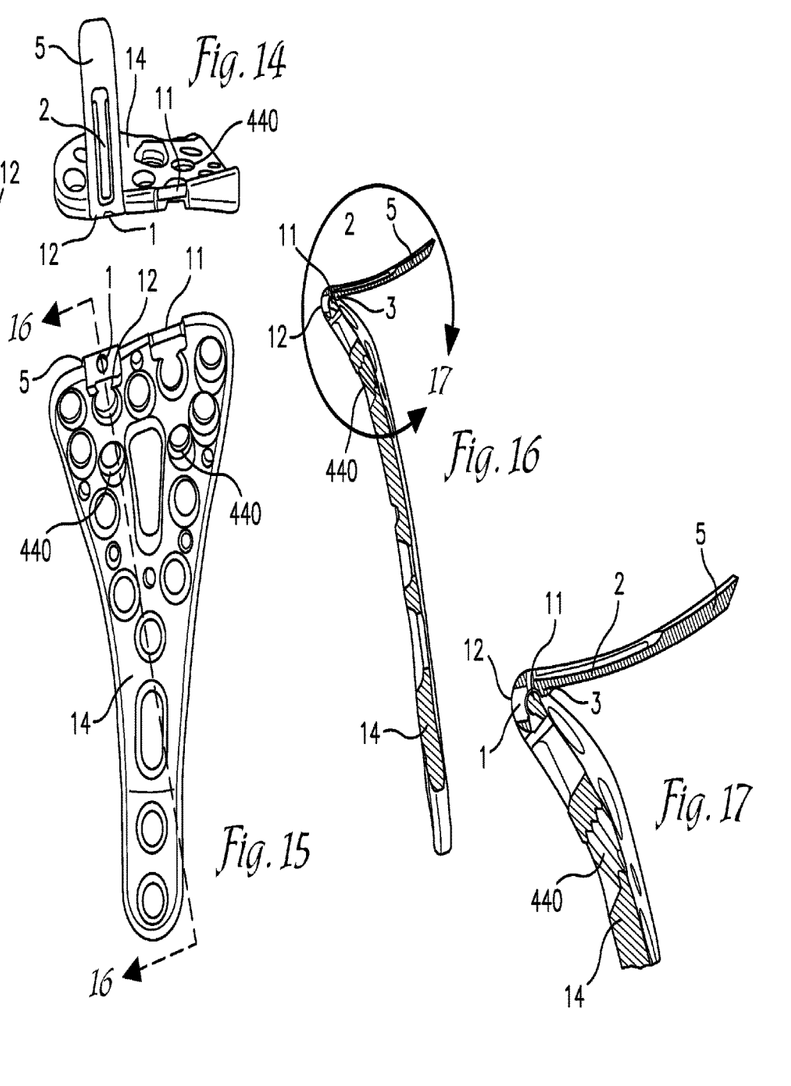
FIG. 14 is a front side view of the beam and the plate of the present inventive concept illustrated in FIG. 13.
FIG. 15 is a top plan view of the beam and the plate of the present inventive concept illustrated in FIG. 13.
FIG. 16 is a left side view of the beam and the plate of the present inventive concept illustrated FIG. 13.
FIG. 17 is a magnified perspective view of portion "F" of FIG. 16 of the beam and the plate of the present inventive concept illustrated in FIG. 16.
Figure 18:
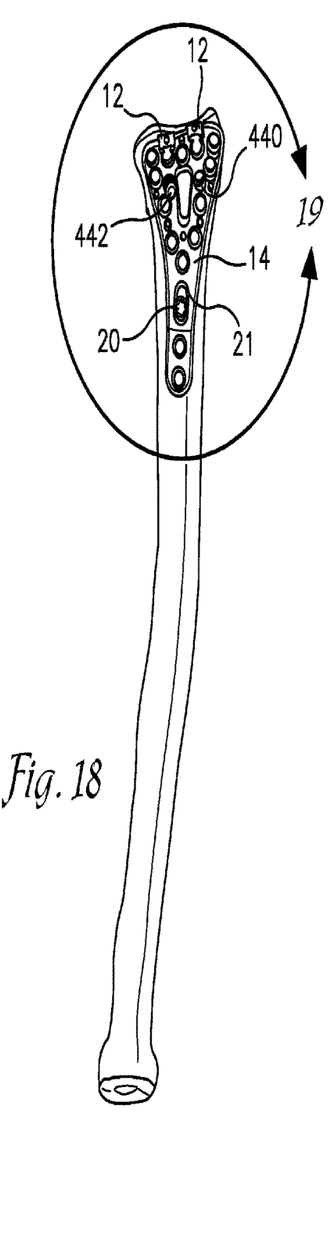
FIG. 18 is a perspective view of the beam illustrated in FIG. 1 in use with a plate of the present inventive concept and mounted to a bone fragment.

At least one positioning device 442, e.g., a screw, is configured to be advanced through one of the openings 440 in the plate 14 and into a portion of a bone, e.g., peri-articular bone fragment 18 as illustrated by FIG. 12, to abut the beam 5 and force the beam 5 to rotate about the axle 11 as the positioning device 442 is further advanced through one of the openings 440. Each of the openings 440 are at least partially threaded to threadably receive and mate with a portion of the positioning device 442 that is at least partially threaded. It is foreseen that each of the openings 440 may receive one of the positioning devices 442 for use with different ones of the beam 5 that are both attached to the plate 14 without deviating from the scope of the present inventive concept. In reducing a fracture, this rotation of the beam 5 can be used to correct the position, e.g., orientation and/or rotation, of a peri-articular bone fragment 18, e.g., from an undesired abnormal fractured position to a desired normal natural position to promote healing of the bone. In one embodiment, the beam 5 can be inserted into the peri-articular portion 18 of bone fragment 19 after the plate 14 is attached to a main portion of the bone fragment 19 with a bone screw 20 placed through an oblong plate hole 21.

As the beam 5 rotates about the axle 11, the bone grip feature 4 of the beam 5 is caused to penetrate the peri-articular portion 18 of bone fragment 19, allowing the beam (5) to rotate further than would be allowed it the bone grip feature 4 had a blunt terminal portion. The tapered design allows the bone grip feature 4 to penetrate the bone fragment 19. The bone grip feature 4 also provides additional bony fixation to promote growth of the bone fragment 19 about the bone grip feature 4 and surrounding areas, which further anchors the beam 5 to the bone fragment 19.

The length of the extractor central rod 8 is longer than the inserter central, rod 15 so that the threads of the extractor central rod can engage past the hole 1 and push upon the axle 11 on the plate 14. By pushing on the axle 11, the extractor central rod 8 forces the beam 5 to back out of its engagement with the axle 11 and disengage therewith. Disengagement of the beam 5 from the axle 11 of the plate 14 is effected by forcing the axle retention feature 3 of the cantilever spring mechanism 2 onto the axle 11, thereby causing the cantilever spring mechanism 2 to move away from the axle 11. With the beam 5 now engaged to the inserter/extractor device 13 and disengaged from the axle 11, the beam 5 can be extracted by withdrawing the inserter/extractor device 13 away from the plate.

The inserter central rod 15 is affixed to the manual rotation device 9 of the inserter/extractor device 13. Using the inserter functionality of the inserter central rod 15, the inserter/extractor device 13 is an assembly of the inserter central rod 15 and manual rotation device 9 inserted into central hole 17 of the handle 10. The handle 10 allows the assembly, i.e., the combination of the inserter central rod 15 and the manual rotation device 9, to rotate freely within the handle 10.

The extractor central rod 8 is affixed to the manual rotation device 9 of the inserter/extractor device 13. Using the extractor functionally, the inserter/extractor device 13 is an assembly composed of the extractor central rod 8 and manual rotation device 9 inserted into the central hole 16 of the inserter/extractor device handle 10. The handle 10 allows assembly, i.e., the combination of the extractor central rod 8 and the manual rotation device 9, to rotate freely within the handle 10.

In one embodiment, the handle 10 of the inserter/extractor device 13 is rounded with and a rectangular shaft 6. The handle 10 and the shaft 6 may be manufactured of the same or different materials. It is foreseen that the handle 10 and/or the shaft 6 may be made of a bioabsorbable material a non-bioabsorbable material, or a combination of both. Further examples of materials for the handle 10 and/or the shaft 6 include, but are not limited to, one or more metals, e.g. a titanium alloy, one or more polymers, and/or one or more laminates.

The beam 5 may be manufactured using a bioabsorbable material, a non-bioabsorbable material, or a combination of both, it is foreseen that the beam 5 may be made of one or more metals, e.g., a titanium alloy, one or more polymers, and/or one or more laminates. In a preferred embodiment, the beam 5 is manufactured using one or more radio-opaque materials to allow visualization of the beam 5 on radiographs, e.g., during or after surgical installation of the beam 5, which view would otherwise be obstructed by, surrounding tissue and the like.

The manual rotation device 9 and the inserter central rod 15 may be comprised of the same or different materials. For example, the manual rotation device 9 and/or the inserter central rod 15 may be made of a bioabsorbable material, a non-bioabsorbable material, or a combination of both. The manual rotation device 9 and/or the inserter central rod 15 may be made of one or more metals, e.g., a titanium alloy, one or more polymers, end/or one or more laminates.

The manual rotation device 9 and the extractor central rod 8 may be made of the same or different materials. For example, the manual rotation device 9 and/or the extractor central rod 8 may be made of a bioabsorbable material, a non-bioabsorbable material, or a combination of both. The manual rotation device 9 and/or the extractor central rod 8 may made of one or more metals, e.g. a titanium alloy, one or more polymers, and/or one or more laminates.

In this manner, the present inventive concept provides a bone fixation system for treating bone fractures that provides the aforementioned advantages over conventional systems as well as other advantages that are apparent in view of this disclosure.

Having now described the features, discoveries and principles of the present inventive aspect of this disclosure, the manner in which the present inventive aspect is constructed and used, the characteristics of the construction and advantageous, new and useful results obtained; the new and useful structures, devices, elements, arrangements, parts and combinations, are set forth in the appended claims.

It is also to be understood that the following claims are intended to cover all of the generic and specific features of the present inventive aspect herein described, and all statements of the scope of the present inventive aspect which, as a matter of language, might be said to fall there between.

What is claimed is:
1. A method of repositioning a displaced bone fragment, the method comprising the steps of:
attaching a rod to a beam, wherein the rod is part of a tool having internal and external portions that are rotatable relative to each other to affect engagement and disen- gagement of the beam with the rod, and wherein the rod is configured to be at least partially received by the beam;

causing the beam to securely engage a portion of a bone fixation plate using the rod; and causing the beam to rotate about the portion of the plate by advancing a positioner at least partially through an opening in the plate.

2. The method according to claim 1, wherein the tool includes a shaft that surrounds a portion of the rod and includes a concave portion configured to abuttingly engage a convex portion of the beam.

3. The method according to claim 1, wherein the plate includes a retention mechanism operable to prevent disengagement of the beam with the plate unless the retention mechanism is biased toward a portion of the plate by the rod.

4. The method according to claim 1, wherein the beam includes a bone fragment-grip feature configured to (i) pierce a bone fragment as the beam rotates relative to the plate, and (ii) provide fixation between the beam and the bone fragment.

5. A method of treating a bone fracture by altering angulation of a fracture fragment of a bone using a bone fixation system, the method comprising the steps of:

securing a beam to a bone fixation plate, wherein the plate has at least one beam engagement feature used for securing the beam to the plate, and wherein the beam has an end portion with (i) a plate engagement feature operable to rotatably engage the at least one beam engagement feature of the plate, (ii) at least one bone engagement feature operable to engage a portion of a bone, and (iii) a retention feature operable to prevent detachment of the beam from the plate;

securing the plate to the fracture fragment of the bone;
advancing a screw through the plate to abut the beam;
causing the beam to pivot with respect to the plate by further advancing the screw through the plate;
wherein the beam includes a receiver comprising a hole extending at least partially through the beam that is operable to receive a tool, and wherein the hole is sized and shaped to threadedly receive a terminally-threaded inserter/extractor rod of the tool, the rod configured to facilitate the securing of the beam to the plate.

6. The method according to claim 5, wherein,
the tool includes internal and external portions that are rotatable relative to each other to affect the engagement and/or disengagement of the beam with the rod, and
the tool includes a shaft that surrounds a portion of the rod and includes a concave portion configured to abuttingly engage a convex portion of the beam.

7. The method according to claim 5, wherein the bone engagement feature is operable to at least partially penetrate the portion of the bone.

8. The method according to claim 5, wherein the plate includes an opening operable to receive a positioner.

9. The method according to claim 8, wherein the opening extends through the plate at an angle that is oblique to a plane defined by a surface of the plate so as to direct the positioner toward an end of the plate having the at least one beam engagement feature.

10. The method according to claim 8, wherein the positioner is a screw operable to threadably advance through the opening and engage a portion of the beam, and cause the beam to pivot relative to the plate.

11. The method according to claim 5, wherein,
the plate includes a retention mechanism operable to prevent disengagement of the beam with the plate unless the retention mechanism is biased toward the portion of the plate by the rod, and
the plate is operable to allow rotation of the beam about the portion of the plate when a positioner is moved with respect to the opening in the plate.

12. The method according to claim 5, wherein,
the at least one beam engagement feature of the plate is an axle that defines an axis of rotation, and
the at least one bone engagement feature and the retention feature of the beam are spaced from each other about a curved portion of the beam that is operable to rotatably engage the axle to permit rotation of the beam relative to the plate about the axis of rotation.

13. The method according to claim 5, wherein the plate includes two beam engagement features that are elongated and extended in a direction substantially parallel to each other on an end of the plate.

* * * * *